(12) United States Patent
Vishnubhotla et al.

(10) Patent No.: US 11,596,527 B2
(45) Date of Patent: Mar. 7, 2023

(54) INTERVERTEBRAL CAGE WITH POROSITY GRADIENT

(71) Applicant: Alphatec Spine, Inc., Carlsbad, CA (US)

(72) Inventors: Sri Vishnubhotla, San Diego, CA (US); Scott Robinson, Encinitas, CA (US); Steven Leong, San Diego, CA (US); Frank Chang, San Marcos, CA (US)

(73) Assignee: Alphatec Spine, Inc., Carlsbad, CA (US)

(*) Notice: Subject to any disclaimer, the term of this patent is extended or adjusted under 35 U.S.C. 154(b) by 212 days.

(21) Appl. No.: 17/174,147

(22) Filed: Feb. 11, 2021

(65) Prior Publication Data

US 2021/0186708 A1    Jun. 24, 2021

Related U.S. Application Data

(63) Continuation of application No. 15/920,898, filed on Mar. 14, 2018, now Pat. No. 10,940,019.
(Continued)

(51) Int. Cl.
*A61F 2/44*    (2006.01)
*A61F 2/30*    (2006.01)

(52) U.S. Cl.
CPC ..... *A61F 2/447* (2013.01); *A61F 2002/30011* (2013.01); *A61F 2002/30028* (2013.01);
(Continued)

(58) Field of Classification Search
CPC combination set(s) only.
See application file for complete search history.

(56) References Cited

U.S. PATENT DOCUMENTS

| 10,940,019 B2 | 3/2021 | Vishnubhotla |
| 2001/0047208 A1 | 11/2001 | Michelson |

(Continued)

FOREIGN PATENT DOCUMENTS

| EP | 0716840 A2 | 6/1996 |
| EP | 3050540 A1 | 8/2016 |

(Continued)

OTHER PUBLICATIONS

Search Report for GB App. No. 1802979.3 dated Jul. 30, 2018.
Search Report for GB App. No. 1804056.8 dated Sep. 6, 2018.

*Primary Examiner* — Sameh R Boles
(74) *Attorney, Agent, or Firm* — Robert Winn (57) ABSTRACT

An intervertebral cage with an outer frame, an open inner core region and a porosity gradient within the outer frame is provided. The outer frame includes a posterior wall, an anterior wall, a pair of side walls extending between the posterior wall and the anterior wall and the porosity gradient may comprise at least one of: a decreasing average pore diameter in a direction from an outer surface to an inner surface of at least one of the pair of side walls; an increasing average pore diameter in a direction from an outer surface to an inner surface of at least one of the pair of side walls; a decreasing average pore diameter in a direction from an upper surface to a lower surface of at least one of the side walls; and an increasing average pore diameter in a direction from an upper surface to a lower surface of at least one of the side walls.

20 Claims, 11 Drawing Sheets

Related U.S. Application Data

(60) Provisional application No. 62/471,128, filed on Mar. 14, 2017.

(52) U.S. Cl.
CPC .............. *A61F 2002/3092* (2013.01); *A61F 2002/3093* (2013.01); *A61F 2002/30593* (2013.01); *A61F 2002/30807* (2013.01); *A61F 2002/30838* (2013.01); *A61F 2002/30904* (2013.01); *A61F 2002/30978* (2013.01); *A61F 2002/30985* (2013.01); *A61F 2310/00359* (2013.01)

(56) References Cited

U.S. PATENT DOCUMENTS

| | | |
|---|---|---|
| 2004/0243237 A1 | 12/2004 | Unwin |
| 2012/0150299 A1 | 6/2012 | Ergun |
| 2013/0325129 A1 | 12/2013 | Huang |
| 2016/0114175 A1* | 4/2016 | Colvin ................ A61N 1/375 607/46 |

FOREIGN PATENT DOCUMENTS

| | | |
|---|---|---|
| WO | 2000041655 A2 | 7/2000 |
| WO | 2003013396 A1 | 2/2003 |
| WO | 2017100366 A1 | 6/2017 |
| WO | 2018081114 A1 | 5/2018 |

\* cited by examiner

INTERVERTEBRAL CAGE WITH POROSITY GRADIENT

RELATED APPLICATIONS

This application is a continuation of U.S. application Ser. No. 15/920,898, filed Mar. 14, 2018, which application claims priority to U.S. Provisional Application No. 62/471,128, filed on Mar. 14, 2017, the contents of each of which are incorporated herein by reference in their entirety.

TECHNICAL FIELD

The present disclosure generally relates to interbody implants, and particularly, to intervertebral cages.

BACKGROUND

Implantable interbody bone grafts such as spinal fusion devices are known and used by surgeons to keep and maintain adjacent vertebrae in a desired spatial relationship, provide weight-bearing support between adjacent vertebral bodies, and promote interbody bone ingrowth and fusion after surgery on a patient. Such spinal fusion devices, sometimes referred to as intervertebral cages, may be used for spine surgical procedures to treat degenerative disk disease, discogenic low back pain, spondylolisthesis, and the like.

Intervertebral cages are formed from a pair of side walls, a posterior wall, and an anterior wall so as to define an open interior for which allograft (donor) or autograft (patient) bone material can be placed to promote the interbody bone ingrowth and fusion. Some intervertebral cages are made from nonporous materials that prevent interbody bone ingrowth and fusion in the wall portions of the cage. Other intervertebral cages have a solid interior made from a porous material, but the porous material in the interior of the cage prevents allograft or autograft bone material from being placed therein and thereby be used to promote bone ingrowth and fusion. Accordingly, an improved intervertebral cage with an open interior and a porous structure that provides weight-bearing support between adjacent vertebral bones and aids in bone ingrowth and fusion would be desirable.

SUMMARY

In one embodiment, an intervertebral cage includes an outer frame with an open inner core region and a porosity gradient within the outer frame. The outer frame includes a posterior wall, an anterior wall, a pair of side walls extending between the posterior wall and the anterior wall, and the porosity gradient may extend through at least one of the pair of side walls of the outer frame. The porosity gradient may comprise a decreasing average pore diameter in a direction from an outer surface to an inner surface of at least one of the pair of side walls or an increasing average pore diameter in a direction from the outer surface to the inner surface of the at least one of the pair of side walls. In the alternative, or in addition to, the porosity gradient may comprise a decreasing average pore diameter in a direction from an upper surface to a lower surface of at least one of the side walls or an increasing average pore diameter in a direction from the upper surface to the lower surface of the at least one of the side walls. Also, the porosity gradient may comprise a decreasing average pore diameter in a direction from the posterior wall to the anterior wall of the outer frame or an increasing average pore diameter in a direction from the posterior wall to the anterior wall of the outer frame.

In some embodiments, the intervertebral cage may have a porosity gradient with an increasing average pore diameter in a direction from the posterior wall to a central portion of at least one of the pair of side walls and in a direction from the anterior wall to the central portion of at least one of the pair of side walls. In other embodiments, the porosity gradient may comprise a decreasing average pore diameter in a direction from the posterior wall to a central portion of at least one of the pair of side walls and in a direction from the anterior wall to the central portion of at least one of the pair of side walls.

The porosity gradient within the intervertebral cage may include a first portion with porosity within a range of about 5% by volume to about 30% by volume and a second portion within a range of about 30% by volume to about 90% by volume. Also, the porosity gradient may include a first portion with porosity with an average diameter between about 5 μm and about 100V and a second portion with porosity with an average diameter between about 100 μm and 1000 μm.

In another embodiment, an intervertebral cage comprises an outer frame with a posterior wall, an anterior wall and a pair of side walls extending between the anterior wall and the posterior wall. An open inner core region is between the posterior wall, the anterior wall and the pair of side walls, and a porosity gradient is within at least one of the posterior wall, the anterior wall and the pair of side walls comprises a porosity gradient. The porosity gradient promotes bone ingrowth and fusion between adjacent vertebrae when the intervertebral cage is inserted between a pair of vertebra during a spine surgery. The porosity gradient may include a first portion with porosity within a range of about 5% by volume to about 30% by volume and a second portion within a range of about 30% by volume to about 90% by volume. In the alternative, or in addition to, the porosity gradient may include a first portion with porosity with an average diameter between about 5 μm and about 100V and a second portion with porosity with an average diameter between about 100 μm and 1000 μm. Also the porosity gradient may comprise at least one of: a decreasing average pore diameter in a direction from an outer surface to an inner surface of at least one of the pair of side walls; an increasing average pore diameter in a direction from an outer surface to an inner surface of at least one of the pair of side walls; a decreasing average pore diameter in a direction from an upper surface to a lower surface of at least one of the side walls; and an increasing average pore diameter in a direction from an upper surface to a lower surface of at least one of the side walls.

In still another embodiment, a method for promoting bone ingrowth and fusion between adjacent vertebrae comprises inserting an intervertebral cage between a pair of adjacent vertebrae during a spine surgical procedure. The intervertebral cage includes an outer frame with a posterior wall, an anterior wall and a pair of side walls extending between the anterior wall and the posterior wall. An open inner core region is between the posterior wall, the anterior wall and the pair of side walls, and a porosity gradient is within at least one of the posterior wall, the anterior wall and the pair of side walls comprises a porosity gradient. The porosity gradient enhances flow of bodily fluids and bone material into the intervertebral cage and promotes bone ingrowth and fusion between adjacent vertebrae. The porosity gradient mat comprise at least of: a decreasing average pore diameter in a direction from an outer surface to an inner surface of at least one of the pair of side walls; an increasing average pore diameter in a direction from an outer surface to an inner surface of at least one of the pair of side walls; a decreasing average pore diameter in a direction from an upper surface to a lower surface of at least one of the side walls; and an increasing average pore diameter in a direction from an upper surface to a lower surface of at least one of the side walls. In some embodiments, the method includes placing allograft or autograft bone material within the open inner core region.

These and additional features provided by the embodiments described herein will be more fully understood in view of the following detailed description in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

DETAILED DESCRIPTION

According to one or more embodiments described herein, an intervertebral cage may generally comprise a pair of side walls, a posterior wall, an interior wall, an open inner core region, and a porosity gradient within at least one of the pair of side walls, posterior wall, and interior wall. The porosity gradient may include porosity at a first location or position within the one of the side walls, posterior wall, and/or interior wall with a first average pore diameter and porosity at a second location or position within the one of the side walls, posterior wall, and/or interior wall with a second average pore diameter that is different than the first average pore diameter. In the alternative, the porosity gradient may include porosity at the first location or position within the one of the side walls, posterior wall, and/or interior wall with a first average pore diameter and porosity at the second location or position within the one of the side walls, posterior wall, and/or interior wall with the same average pore diameter as the first average pore diameter, however the number or density of pores at the second location or position is different than the number or density of pores at the first location. Various embodiments of intervertebral cages will be described in further detail herein with specific reference to the appended drawings.

Figure 1:
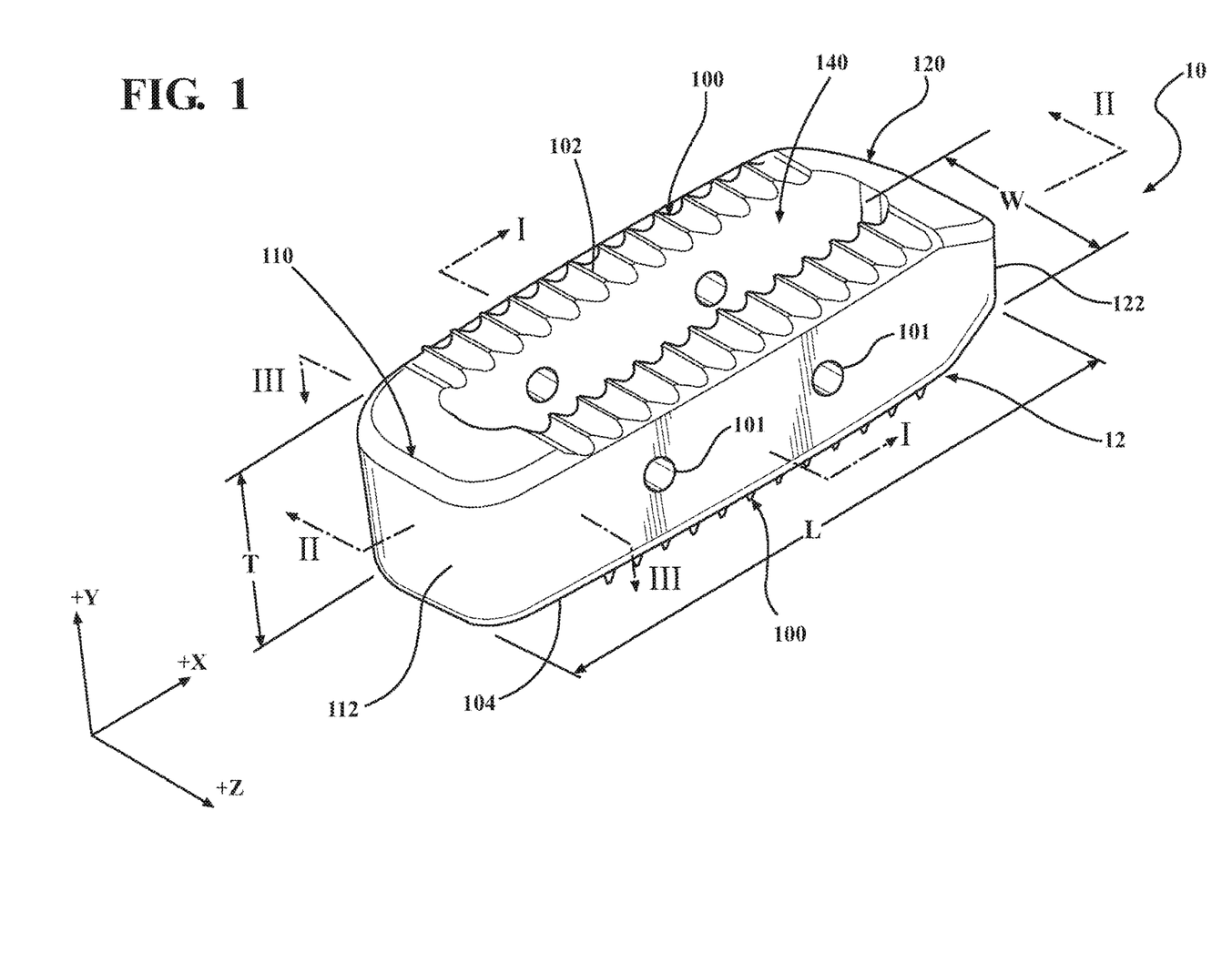
FIG. 1 depicts a perspective view of an intervertebral cage according to one or more embodiments described herein.

FIG. 1 generally depicts one embodiment of an intervertebral cage 10 with an outer frame 12 with a pair of side walls 100, a posterior wall 110, and an anterior wall 120. An open inner core region 140 is provided within the outer frame 12. The intervertebral cage 10 has an upper surface 102 (+Y direction), a lower surface 104 (−Y direction), a posterior end 112, and an anterior end 122. Also, each of the side walls 100 have an outer surface 106 distal to the open inner core region 140 and an inner surface 108 proximal to the open inner core region 140.

At least one of the side walls 100, posterior wall 110 and/or anterior wall 120 has a porosity gradient (not shown in FIG. 1) that assists in bone ingrowth and fusion when the intervertebral cage 10 is used and placed between adjacent vertebrae of a patient during a surgical procedure. As used herein, the term "porosity" refers to void space in volume percent within a matrix of material used to form the intervertebral cage 10 and the phrase "porosity gradient" refers to a change in porosity as a function of distance (e.g., thickness, width, and/or length) within the intervertebral cage 10. Also, allograft or autograft bone material may be placed within the open inner core region 140 to promote bone ingrowth and fusion. In some embodiments, at least one of the side walls 100 includes one or more apertures 101 through which allograft or autograft bone material can be placed into the open inner core region 140 to promote bone ingrowth and fusion. Accordingly, the intervertebral cage 10 without allograft or autograft bone material within the open inner core region 140 may be positioned between a pair of adjacent vertebra during spine surgery, and then the open inner core region 140 may be filled with allograft or autograft bone material utilizing the one or more apertures 101. In the alternative, the intervertebral cage 10 with allograft or autograft bone material within the open inner core region 140 may be positioned between a pair of adjacent vertebra during spine surgery, and additional allograft or autograft bone material may optionally be inserted into the open inner core region 140.

In embodiments, at least one of the side walls 100, posterior wall 110 and/or anterior wall 120 of the intervertebral cage 10 has one or more portions with porosity within the range of about 10% to about 80% by volume with open pores distributed throughout. For example, the at least one of the side walls 100, posterior wall 110 and/or anterior wall 120 of the intervertebral cage 10 may have one or more portions with porosity within the range of about 10% to about 80% by volume with open pores distributed throughout. In some embodiments, at least one of the side walls 100, posterior wall 110 and/or anterior wall 120 of the intervertebral cage 10 has a first portion with a porosity within the range of about 5% to about 30% by volume, for example within the range of about 5% to about 10% by volume, and a second portion with a porosity within the range of about 30% to about 90% by volume, for example within the range of about 75% to about 90% by volume. The average pore diameter of the porosity may range from about 1 micron to about 1500 microns. For example, the average pore diameter of the porosity may range from about 1 micron to about 500 microns. In another example, the average pore diameter of the porosity may range from about 5 microns to about 500 microns. As used herein, the phrase "average pore diameter" refers to an average of the diameters of at least ten (10) pores on a selected plane along a thickness, width or length of the intervertebral cage 10 and the term "diameter" refers to an average diameter of a pore obtained by an average of at least two diameter measurements of the pore.

In some embodiments, the intervertebral cage 10 has a first portion with a first average pore diameter and a second portion with a second average pore diameter that is different than the first average pore diameter such that the porosity of the first portion is different than the porosity of the second portion. In other embodiments, the intervertebral cage 10 has a first portion with a first average pore diameter and a second portion with a second average pore diameter that is the same as the first average pore diameter, however the number of pores in the second portion is different than the number of pores in the first portion such that the porosity of the first portion is different than the porosity of the second portion.

Figure 2A:
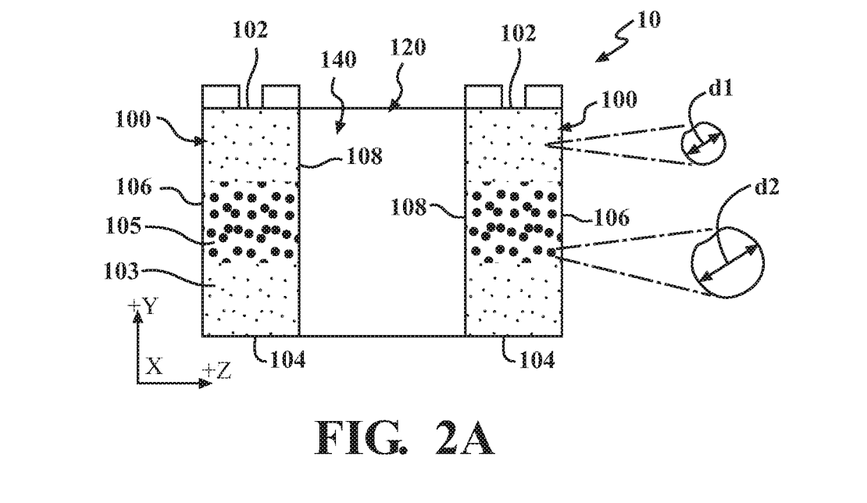
FIG. 2A schematically depicts a cross-sectional view of section I-I of the intervertebral cage in FIG. 1 with a porosity gradient according to one or more embodiments described herein.
Figure 2B:
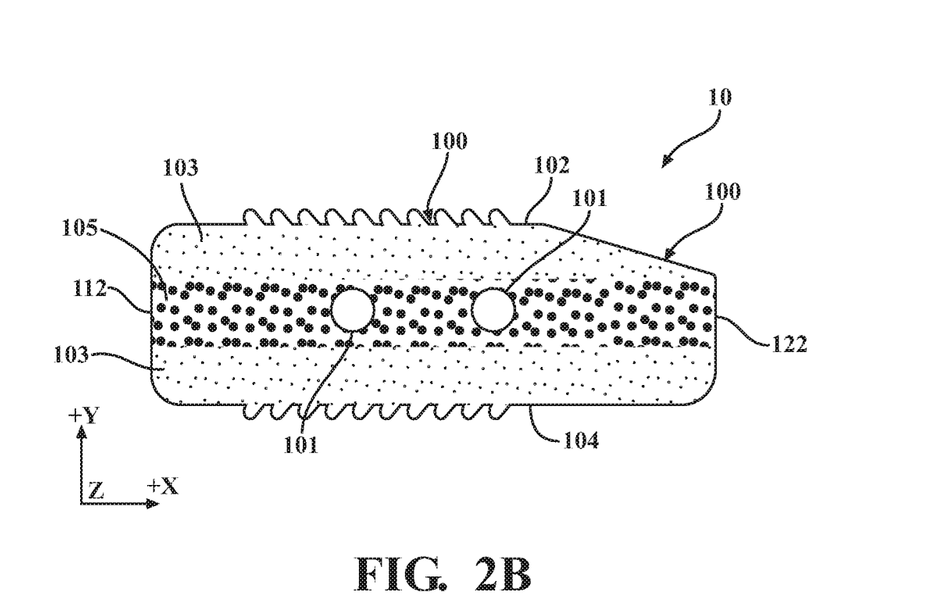
FIG. 2B schematically depicts a cross-sectional view of section II-II of the intervertebral cage in FIG. 1 with the porosity gradient depicted in FIG. 2A.

Referring now to FIGS. 2A-2B, an embodiment of a porosity gradient along a thickness (Y direction) of the side walls 100 is schematically depicted. Particularly, an end cross-sectional view depicted by section I-I in FIG. 1 is schematically depicted in FIG. 2A and a side cross-sectional view depicted by section II-II in FIG. 1 is schematically depicted in FIG. 2B. Each of the side walls 100 comprise a first portion 103 with porosity having a first average pore diameter d1 and a second portion 105 with porosity having a second average pore diameter d2 that is greater than the first average pore diameter d1 (i.e., d2>d1). As depicted in FIGS. 2A-2B, the first portion 103 may extend from the upper surface 102 towards the lower surface 104 and the second portion 105 is positioned below (−Y direction) the first portion 103. In embodiments, each of the side walls 100 comprises an upper (+Y direction) first portion 103 extending from the upper surface 102 towards the lower surface 104, a lower (−Y direction) first portion 103 extending from the lower surface 104 towards the upper surface 102, and a second portion 105 positioned between the upper and lower first portions 103. Accordingly, a porosity gradient is provided along the thickness (Y direction) of the side walls 100 with the second portion 105 with porosity having the second average pore diameter d2 sandwiched between the upper and lower first portions 103 with porosity having the first average pore diameter d1 that is less than the second average pore diameter d2. In some embodiments, the first portion 103, and other first portions described herein, may have a porosity within the range of about 5% to about 30% by volume, for example within the range of about 5% to about 10% by volume, and the second portion 105, and other second portions described herein, may have a porosity within the range of about 30% to about 90% by volume, for example within the range of about 75% to about 90% by volume. Also, while FIGS. 2A-2B schematically depict three separate porosity portions, i.e., two first portions 103 and one second portion 105, it should be understood that the porosity gradient along the thickness of the side walls 100 may be formed from only two separate porosity portions, i.e., only one first portion 103 and one second portion 105, more than three separate porosity portions, or a single porosity portion with a pores comprising a gradual or continuous change in pore diameter as a function of thickness of the side walls 100.

Figure 3A:
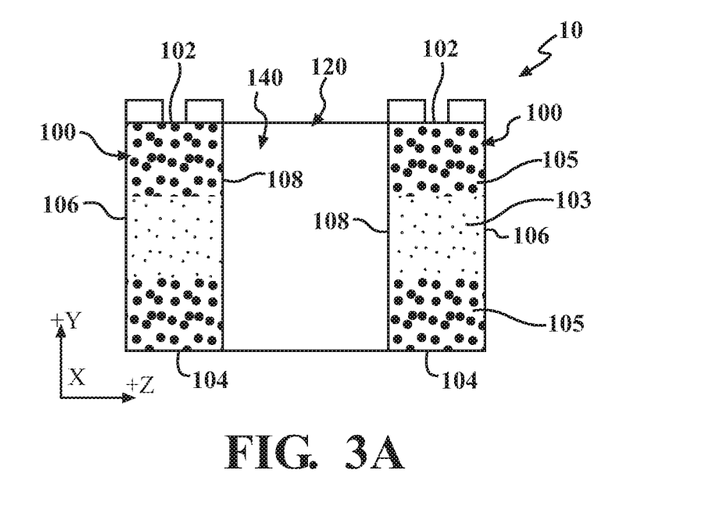
FIG. 3A schematically depicts a cross-sectional view of section I-I of the intervertebral cage in FIG. 1 with a porosity gradient according to one or more embodiments described herein.
Figure 3B:
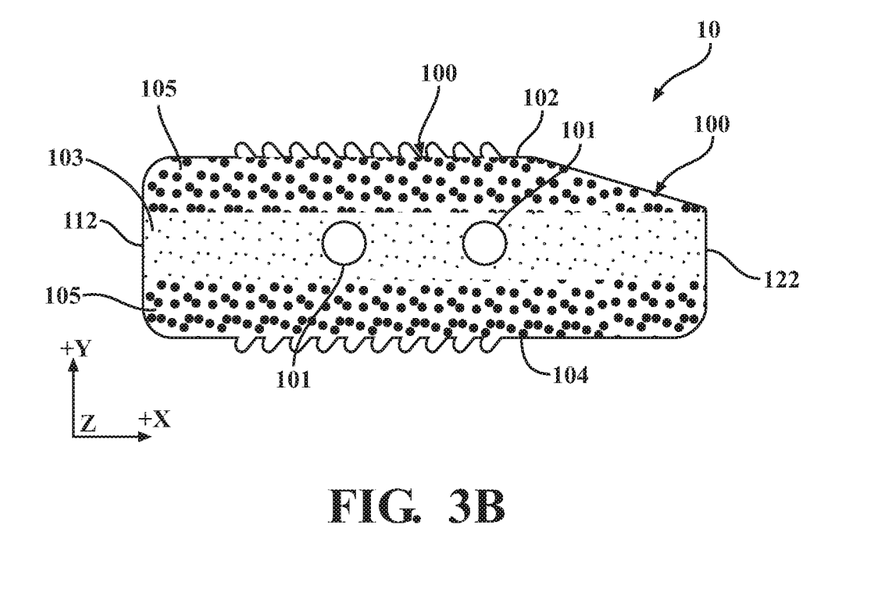
FIG. 3B schematically depicts a cross-sectional view of section II-II of the intervertebral cage in FIG. 1 with the porosity gradient depicted in FIG. 3A.

Referring now to FIGS. 3A-3B, another embodiment of a porosity gradient along a thickness (Y direction) of the side walls 100 is schematically depicted. Particularly, the end cross-sectional view depicted by section I-I in FIG. 1 is schematically depicted in FIG. 3A and the side cross-sectional view depicted by section II-II in FIG. 1 is schematically depicted in FIG. 3B. Each of the side walls 100 comprise a first portion 103 with porosity having a first average pore diameter d1 (FIG. 2A) and a second portion 105 with porosity having a second average pore diameter d2 (FIG. 2A) that is greater than the first average pore diameter d1. As depicted in FIGS. 3A-3B, the second portion 105 may extend from the upper surface 102 towards the lower surface 104. Also, the first portion 103 is positioned below (−Y direction) the second portion 105. In embodiments, each of the side walls 100 comprises an upper (+Y direction) second portion 105 extending from the upper surface 102 towards the lower surface 104, a lower (−Y direction) second portion 105 extending from the lower surface 104 towards the upper surface 102, and a first portion 103 positioned between the upper and lower second portions 105. Accordingly, a porosity gradient is provided along the thickness (Y direction) of the side walls 100 with a first portion 103 with porosity having the first average pore diameter d1 sandwiched between upper and lower second portions 105 with porosity having the second average pore diameter d2 that is greater than the first average pore diameter d1.

Figure 4A:
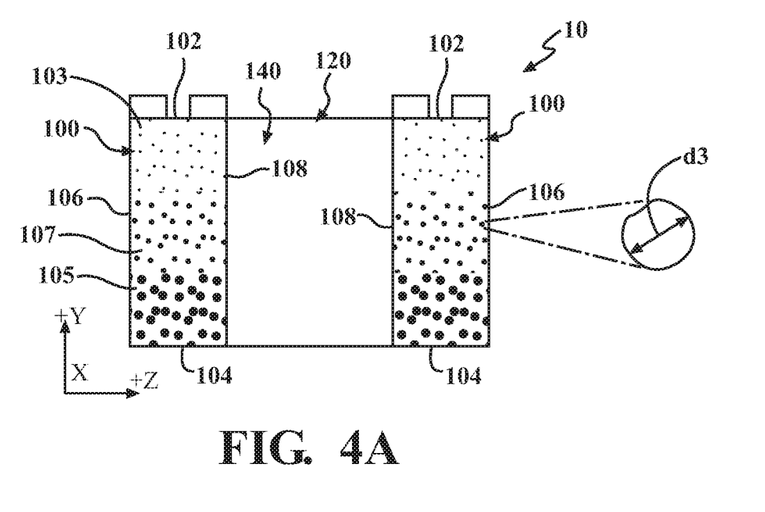
FIG. 4A schematically depicts a cross-sectional view of section I-I of the intervertebral cage in FIG. 1 with a porosity gradient according to one or more embodiments described herein.
Figure 4B:
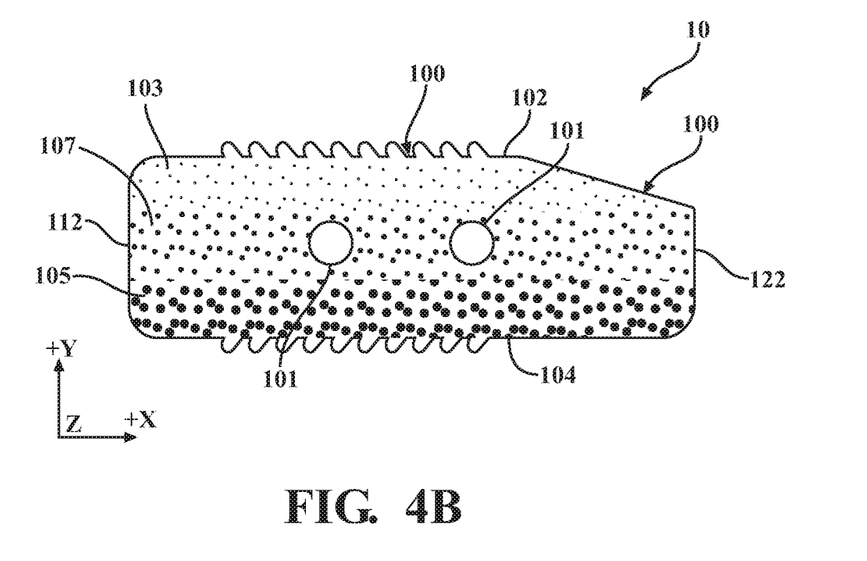
FIG. 4B schematically depicts a cross-sectional view of section II-II of the intervertebral cage in FIG. 1 with the porosity gradient depicted in FIG. 4A.

Referring now to FIGS. 4A-4B, yet another embodiment of a porosity gradient along a thickness (Y direction) of the side walls 100 is schematically depicted. Particularly, the end cross-sectional view depicted by section I-I in FIG. 1 is schematically depicted in FIG. 4A and the side cross-sectional view depicted by section II-II in FIG. 1 is schematically depicted in FIG. 4B. Each of the side walls 100 comprise a first portion 103 with porosity having a first average pore diameter d1 (FIG. 2A), a second portion 105 with porosity having a second average pore diameter d2 (FIG. 2A) that is greater than the first average pore diameter d1, and a third portion 107 with porosity having a third average pore diameter d3 that is greater than the first average pore diameter d1 and less than the second average pore diameter d2 (i.e., d1<d3<d2). In some embodiments, the third portion 107, and other third portions described herein, may have porosity between the range of porosity of the first portion 103 and the range of porosity of the second portion 105. For example, the third portion may have porosity within the range of about 5% to about 90% by volume, for example within the range of about 10% to about 75% by volume. In embodiments, where the first portion 103 has porosity within the range of about 5% to about 10% by volume and the second portion 105 has porosity within the range of about 75% to about 90% by volume, the third portion 107 may have porosity within the range of about 10% to about 75% by volume.

Still referring to FIGS. 4A-4B, the first portion 103 may extend from the upper surface 102 towards the lower surface 104, the second portion 105 may extend from the lower surface 104 towards the upper surface 102, and the third portion 107 is positioned between the first portion 103 and the second portion 105. Accordingly, a porosity gradient is provided along the thickness (Y direction) of the side walls 100 with a third portion 107 with porosity having the third average pore diameter d3 sandwiched between a first portion with porosity having the first average pore diameter d1 that is less than the third average pore diameter d3 (i.e., d1<d3) and a second portion with porosity having the second average pore diameter d2 that is greater than the third average pore diameter d3 (i.e., d2>d3).

Figure 5A:
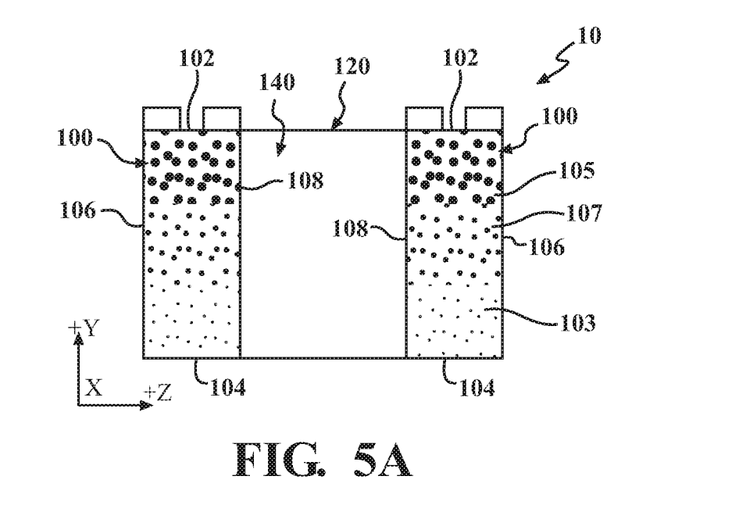
FIG. 5A schematically depicts a cross-sectional view of section I-I of the intervertebral cage in FIG. 1 with a porosity gradient according to one or more embodiments described herein.
Figure 5B:
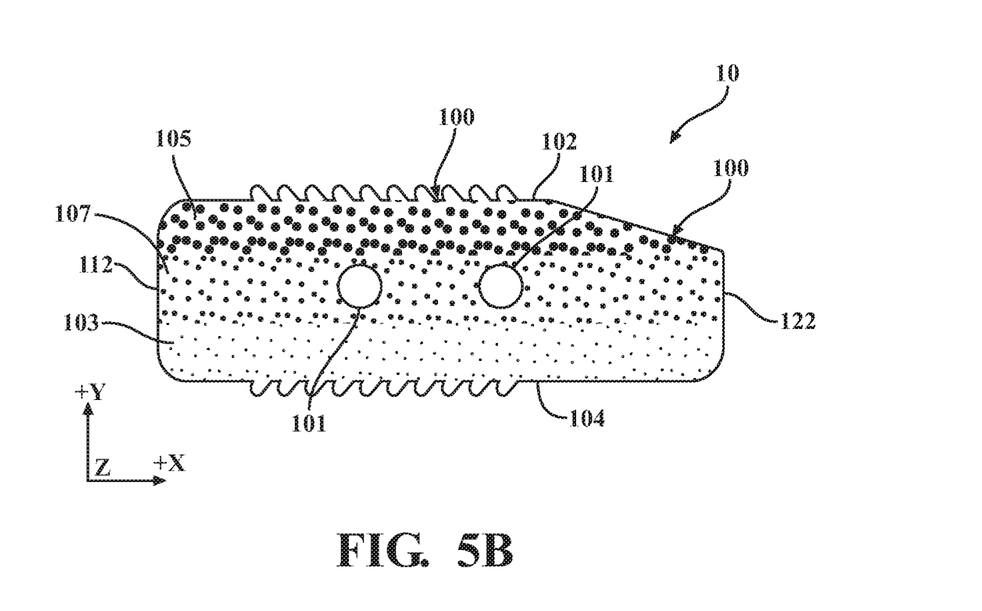
FIG. 5B schematically depicts a cross-sectional view of section II-II of the intervertebral cage in FIG. 1 with the porosity gradient depicted in FIG. 5A.

Referring now to FIGS. 5A-5B, still yet another embodiment of a porosity gradient along a thickness (Y direction) of the side walls 100 is schematically depicted. Particularly, the end cross-sectional view depicted by section I-I in FIG. 1 is schematically depicted in FIG. 5A and the side cross-sectional view depicted by section II-II in FIG. 1 is schematically depicted in FIG. 5B. Each of the side walls 100 comprise a first portion 103 with porosity having a first average pore diameter d1 (FIG. 2A), a second portion 105 with porosity having a second average pore diameter d2 (FIG. 2A) that is greater than the first average pore diameter d1, and a third portion 107 with porosity having a third average pore diameter d3 (FIG. 4A) that is greater than the first average pore diameter d1 and less than the second average pore diameter d2 (i.e., d1<d3<d2). As depicted in FIGS. 5A-5B, the second portion 105 may extend from the upper surface 102 towards the lower surface 104, the first portion 103 may extend from the lower surface 104 towards the upper surface 102, and the third portion 107 is positioned between the second portion 105 and the first portion 103. Accordingly, a porosity gradient is provided along the thickness (Y direction) of the side walls 100 with a third portion 107 with porosity having the third average pore diameter d3 sandwiched between a second portion 105 with porosity having the second average pore diameter d2 that is greater than the third average pore diameter d3 (i.e., d2>d3) and a first portion 103 with porosity having the first average pore diameter d1 that is less than the third average pore diameter d3 (i.e., d1<d3).

Figure 6A:
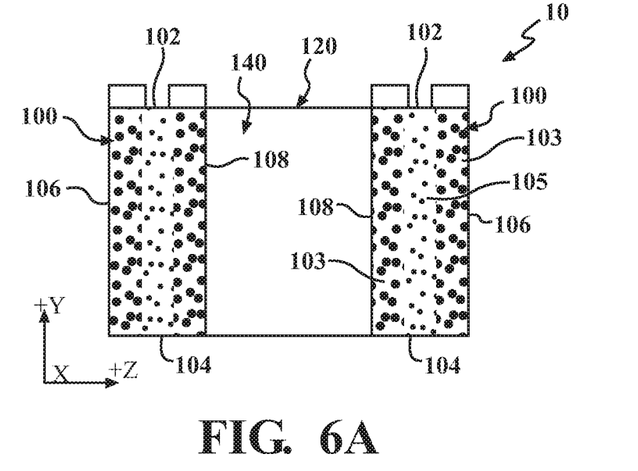
FIG. 6A schematically depicts a cross-sectional view of section I-I of the intervertebral cage in FIG. 1 with a porosity gradient according to one or more embodiments described herein.
Figure 6B:
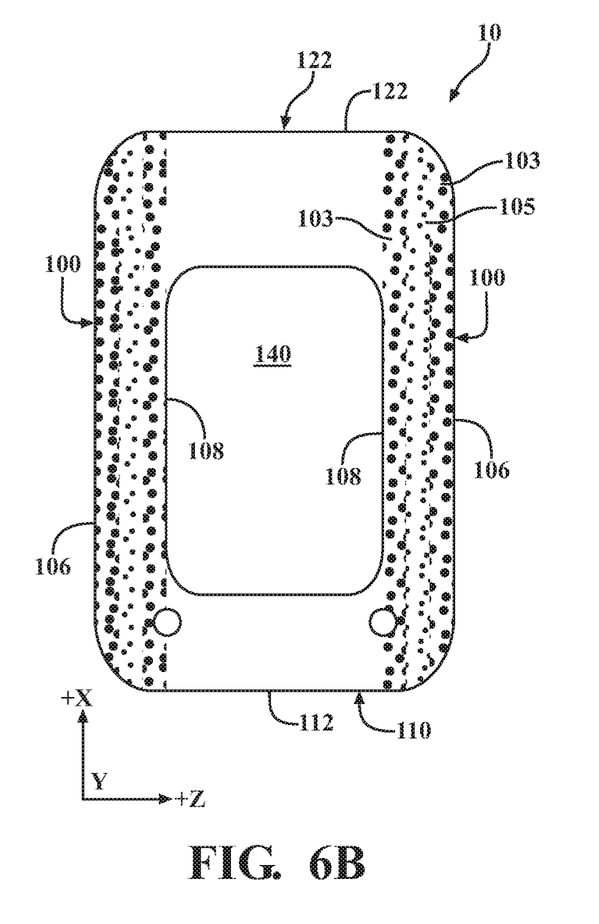
FIG. 6B schematically depicts a cross-sectional view of section of the intervertebral cage in FIG. 1 with the porosity gradient depicted in FIG. 6A.

Referring now to FIGS. 6A-6B, an embodiment of a porosity gradient along a width (Z direction) of the side walls 100 is schematically depicted. Particularly, an end cross-sectional view depicted by section I-I in FIG. 1 is schematically depicted in FIG. 6A and a top cross-sectional view depicted by section in FIG. 1 is schematically depicted in FIG. 6B. Each of the side walls 100 comprise a first portion 103 with porosity having a first average pore diameter d1 (FIG. 2A) and a second portion 105 with porosity having a second average pore diameter d2 (FIG. 2A) that is greater than the first average pore diameter d1 (i.e., d2>d1). As depicted in FIGS. 6A-6B, the first portion 103 may extend from the outer surface 106 towards the inner surface 108 and the second portion 105 may be positioned inwardly toward the open inner core region 140 from the first portion 103. In embodiments, each of the side walls 100 comprises an outer first portion 103 extending from the outer surface 106 towards the inner surface 108, an inner first portion 103 extending from the inner surface 108 towards the outer surface 106, and a second portion 105 positioned between the outer and inner first portions 103. Accordingly, a porosity gradient is provided along the width (Z direction) of the side walls 100 with the second portion 105 with porosity having the second average pore diameter d2 sandwiched between the outer and inner first portions 103 with porosity having the first average pore diameter d1 that is less than the second average pore diameter d2.

Figure 7A:
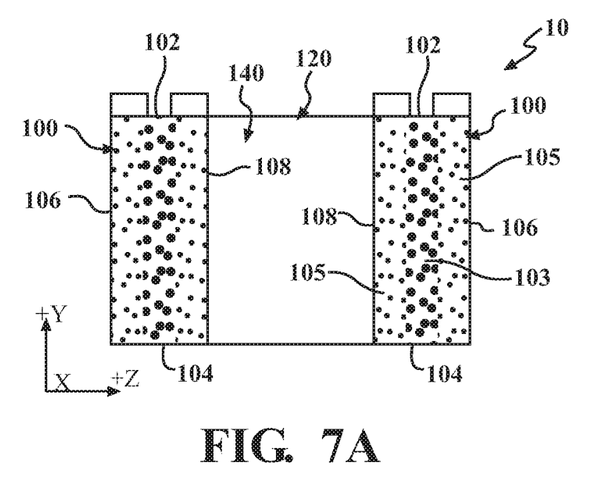
FIG. 7A schematically depicts a cross-sectional view of section I-I of the intervertebral cage in FIG. 1 with a porosity gradient according to one or more embodiments described herein.
Figure 7B:
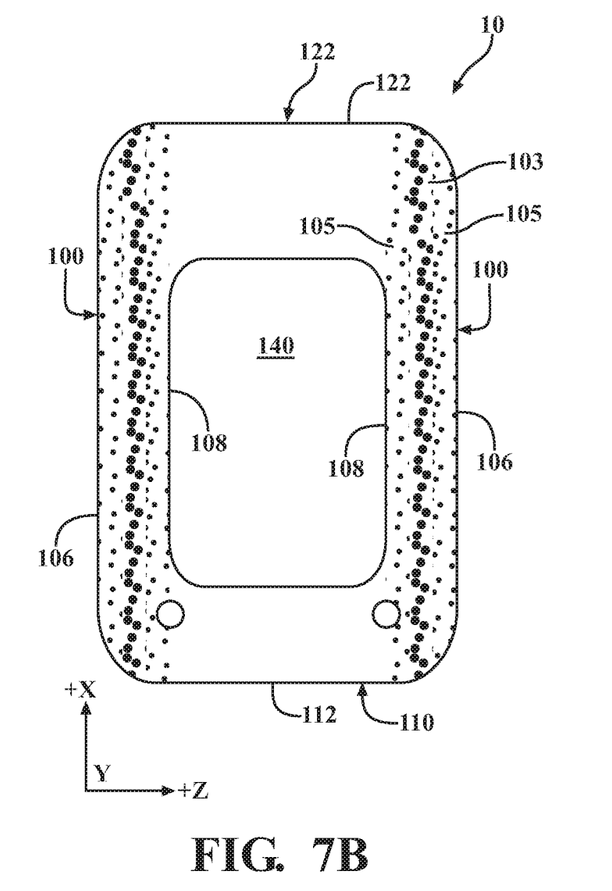
FIG. 7B schematically depicts a cross-sectional view of section of the intervertebral cage in FIG. 1 with the porosity gradient depicted in FIG. 7A.

Referring now to FIGS. 7A-7B, another embodiment of a porosity gradient along a width (Z direction) of the side walls 100 is schematically depicted. Particularly, an end cross-sectional view depicted by section I-I in FIG. 1 is schematically depicted in FIG. 7A and a top cross-sectional view depicted by section in FIG. 1 is schematically depicted in FIG. 7B. Each of the side walls 100 comprise a first portion 103 with porosity having a first average pore diameter d1 (FIG. 2A) and a second portion 105 with porosity having a second average pore diameter d2 (FIG. 2A) that is greater than the first average pore diameter d1 (i.e., d2>d1). As depicted in FIGS. 7A-7B, the second portion 105 may extend from the outer surface 106 towards the inner surface 108 and the first portion 103 may be positioned inwardly toward the open inner core region 140 from the second portion 105. In embodiments, each of the side walls 100 comprises an outer second portion 105 extending from the outer surface 106 towards the inner surface 108, an inner second portion 105 extending from the inner surface 108 towards the outer surface 106, and a first portion 103 positioned between the outer and inner second portions 105. Accordingly, a porosity gradient is provided along the width (Z direction) of the side walls 100 with the first portion 103 with porosity having the first average pore diameter d1 sandwiched between the outer and inner second portions 105 with porosity having the second average pore diameter d2 that is greater than the first average pore diameter d1.

Figure 8A:
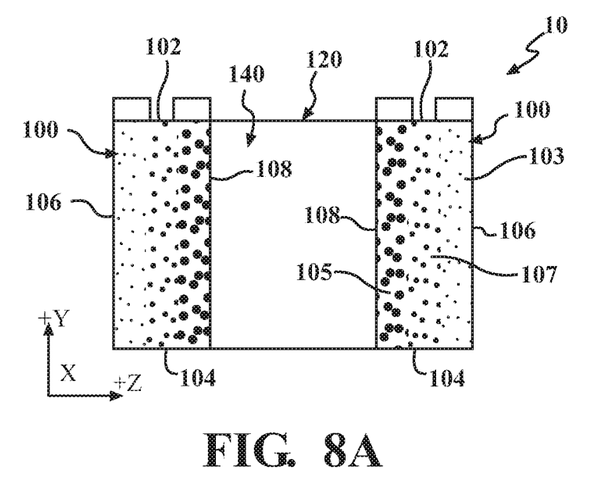
FIG. 8A schematically depicts a cross-sectional view of section I-I of the intervertebral cage in FIG. 1 with a porosity gradient according to one or more embodiments described herein.
Figure 8B:
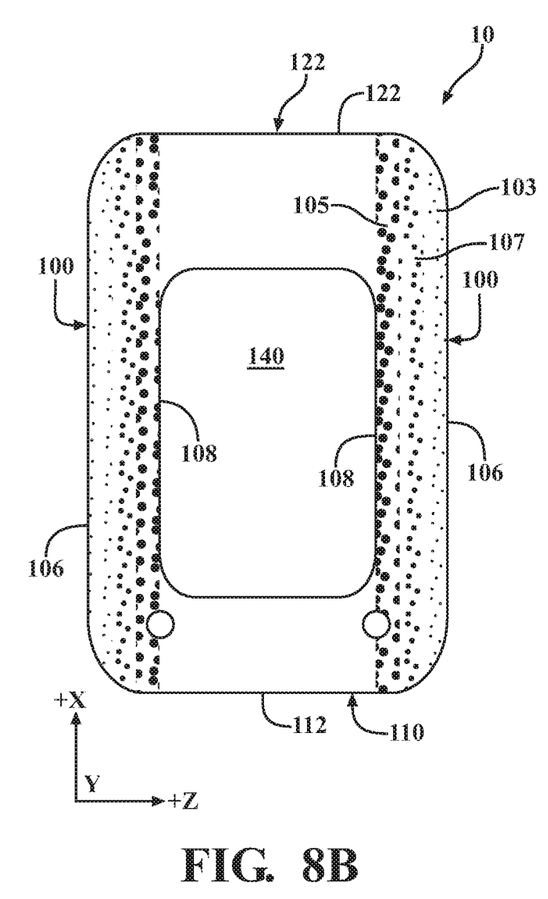
FIG. 8B schematically depicts a cross-sectional view of section of the intervertebral cage in FIG. 1 with the porosity gradient depicted in FIG. 8A.

Referring now to FIGS. 8A-8B, yet another embodiment of a porosity gradient along a width (Z direction) of the side walls 100 is schematically depicted. Particularly, the end cross-sectional view depicted by section I-I in FIG. 1 is schematically depicted in FIG. 8A and the top cross-sectional view depicted by section in FIG. 1 is schematically depicted in FIG. 8B. Each of the side walls 100 comprise a first portion 103 with porosity having a first average pore diameter d1 (FIG. 2A), a second portion 105 with porosity having a second average pore diameter d2 (FIG. 2A) that is greater than the first average pore diameter d1, and a third portion 107 with porosity having a third average pore diameter d3 (FIG. 4A) that is greater than the first average pore diameter d1 and less than the second average pore diameter d2 (i.e., d1<d3<d2). As depicted in FIGS. 8A-8B, the first portion 103 may extend from the outer surface 106 towards the inner surface 108, the second portion 105 may extend from the inner surface 108 towards the outer surface 106, and the third portion 107 may be positioned between the first portion 103 and the second portion 105. Accordingly, a porosity gradient is provided along the width (Z direction) of the side walls 100 with the third portion 107 with porosity having the third average pore diameter d3 sandwiched between the first portion with porosity having the first average pore diameter d1 that is less than the third average pore diameter d3 (i.e., d1<d3) and the second portion 105 with porosity having the second average pore diameter d2 that is greater than the third average pore diameter d3 (i.e., d2>d3).

Figure 9A:
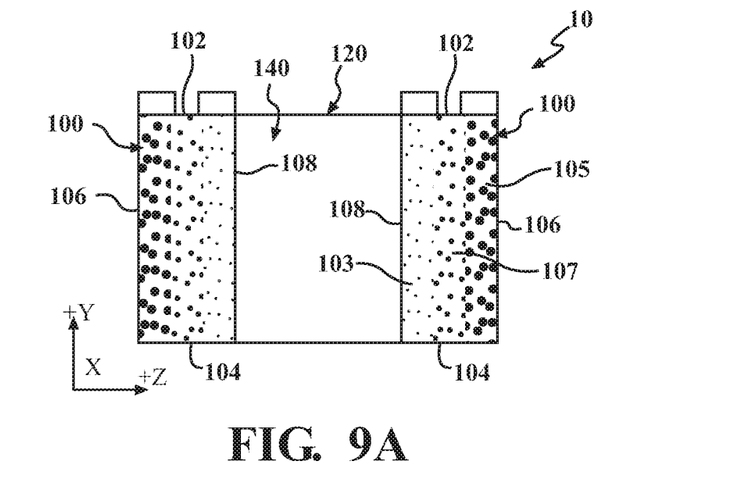
FIG. 9A schematically depicts a cross-sectional view of section I-I of the intervertebral cage in FIG. 1 with a porosity gradient according to one or more embodiments described herein.
Figure 9B:
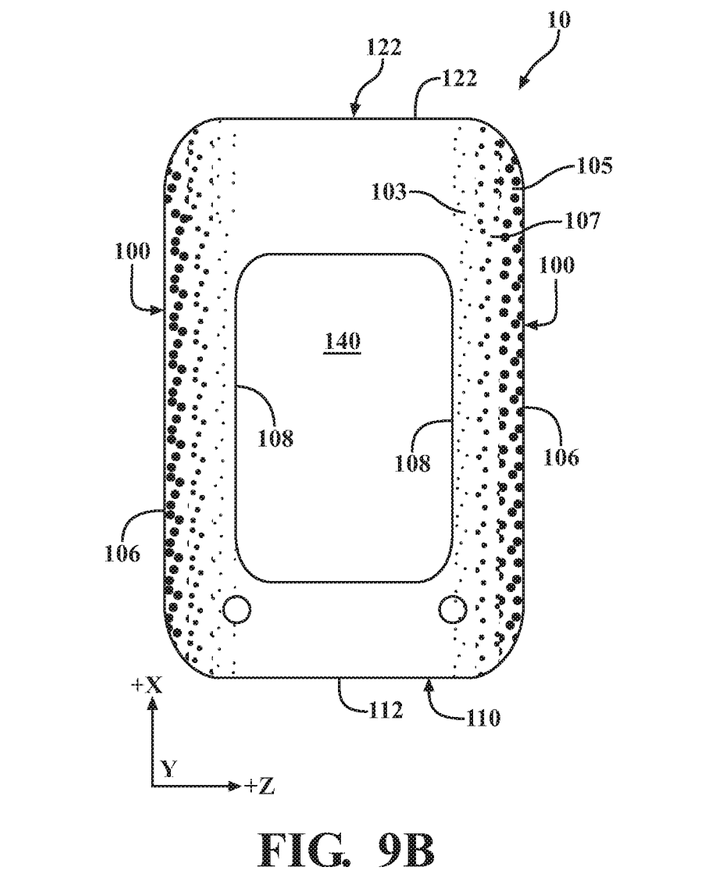
FIG. 9B schematically depicts a cross-sectional view of section of the intervertebral cage in FIG. 1 with the porosity gradient depicted in FIG. 9A.

Referring now to FIGS. 9A-9B, still yet another embodiment of a porosity gradient along a width (Z direction) of the side walls 100 is schematically depicted. Particularly, the end cross-sectional view depicted by section I-I in FIG. 1 is schematically depicted in FIG. 9A and the top cross-sectional view depicted by section in FIG. 1 is schematically depicted in FIG. 9B. Each of the side walls 100 comprise a first portion 103 with porosity having a first average pore diameter d1 (FIG. 2A), a second portion 105 with porosity having a second average pore diameter d2 (FIG. 2A) that is greater than the first average pore diameter d1, and a third portion 107 with porosity having a third average pore diameter d3 (FIG. 4A) that is greater than the first average pore diameter d1 and less than the second average pore diameter d2 (i.e., d1<d3<d2). As depicted in FIGS. 9A-9B, the second portion 105 may extend from the outer surface 106 towards the inner surface 108, the first portion 103 may extend from the inner surface 108 towards the outer surface 106, and the third portion 107 may be positioned between the second portion 105 and the first portion 103. Accordingly, a porosity gradient is provided along the width (Z direction) of the side walls 100 with the third portion 107 with porosity having the first average pore diameter d3 sandwiched between the second portion 105 with porosity having the second average pore diameter d2 that is greater than the third average pore diameter d3 (i.e., d2>d3) and the first portion 103 with porosity having the second average pore diameter d1 that is less than the third average pore diameter d3 (i.e., d1<d3).

Figure 10A:
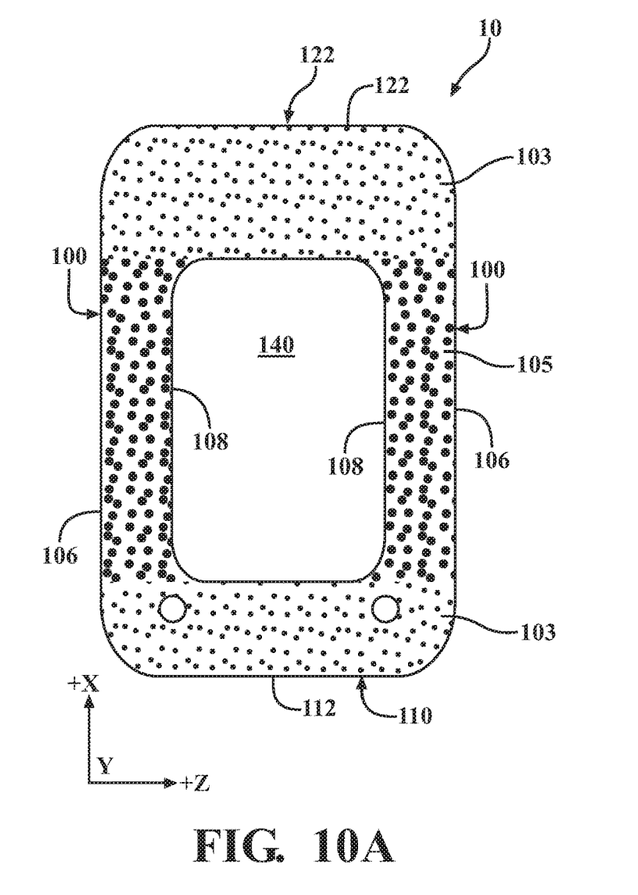
FIG. 10A schematically depicts a cross-sectional view of section of the intervertebral cage in FIG. 1 with a porosity gradient according to one or more embodiments described herein.
Figure 10B:
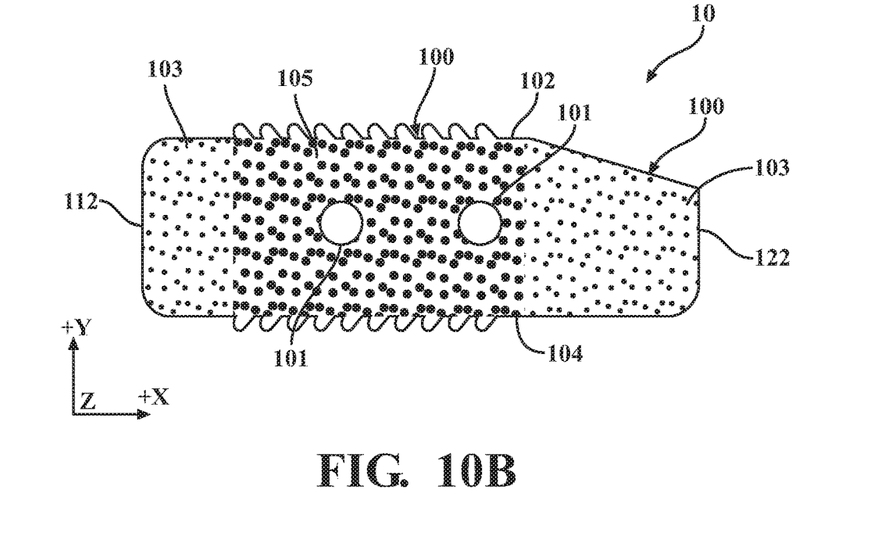
FIG. 10B schematically depicts a cross-sectional view of section II-II of the intervertebral cage in FIG. 1 with the porosity gradient depicted in FIG. 10A.

Referring now to FIGS. 10A-10B, an embodiment of a porosity gradient along a length (X direction) of the intervertebral cage 10 is schematically depicted. Particularly, a top cross-sectional view depicted by section in FIG. 1 is schematically depicted in FIG. 10A and a side cross-sectional view depicted by section II-II in FIG. 1 is schematically depicted in FIG. 10B. A first portion 103 with porosity having a first average pore diameter d1 (FIG. 2A) and a second portion 105 with porosity having a second average pore diameter d2 (FIG. 2A) that is greater than the first average pore diameter d1 (i.e., d2>d1) extend along a length of the intervertebral cage. As depicted in FIGS. 10A-10B, the first portion 103 may extend from the posterior end 112 towards the anterior end 122. Also, the second portion 105 is positioned between the first portion and the anterior end 122. In embodiments, the length of the intervertebral cage 10 comprises a posterior first portion 103 extending from the posterior end 112 towards the anterior end 122, an anterior first portion 103 extending from the anterior end 122 towards the posterior end 112, and a second portion 105 positioned between the posterior and anterior first portions 103. Accordingly, a porosity gradient is provided along the length (X direction) of the intervertebral cage 10 with a second portion 105 with porosity having the second average pore diameter d2 sandwiched between posterior and anterior first portions 103 with porosity having the first average pore diameter d1 that is less than the second average pore diameter d2.

Figure 11A:
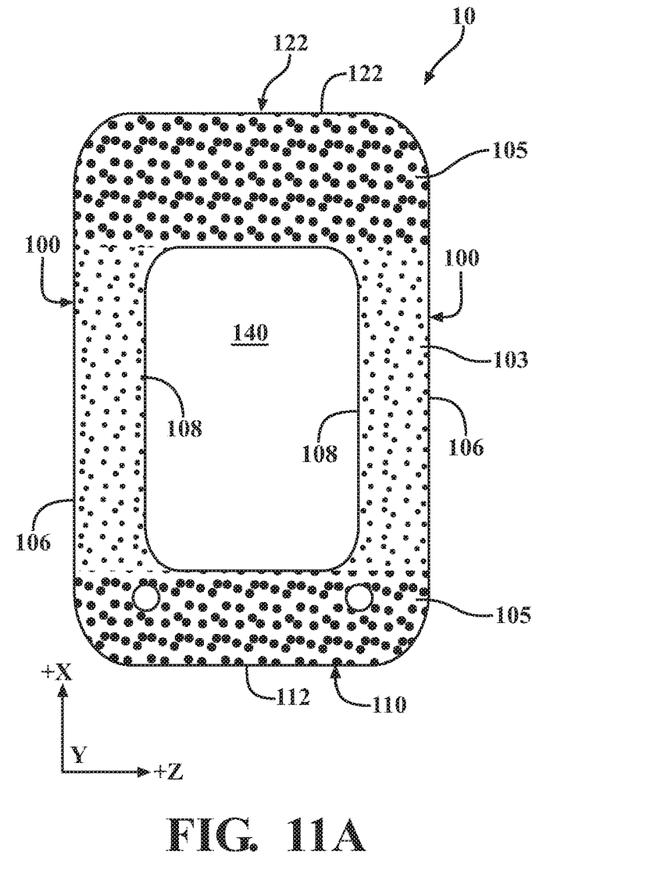
FIG. 11A schematically depicts a cross-sectional view of section of the intervertebral cage in FIG. 1 with a porosity gradient according to one or more embodiments described herein.
Figure 11B:
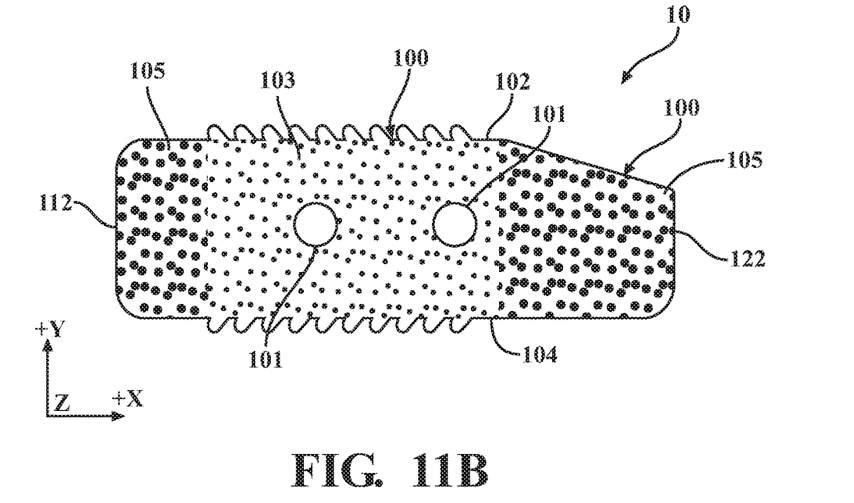
FIG. 11B schematically depicts a cross-sectional view of section II-II of the intervertebral cage in FIG. 1 with the porosity gradient depicted in FIG. 11A.

Referring now to FIGS. 11A-11B, another embodiment of a porosity gradient along a length (X direction) of the intervertebral cage 10 is schematically depicted. Particularly, a top cross-sectional view depicted by section in FIG. 1 is schematically depicted in FIG. 11A and a side cross-sectional view depicted by section II-II in FIG. 1 is schematically depicted in FIG. 11B. A first portion 103 with porosity having a first average pore diameter d1 and a second portion 105 with porosity having a second average pore diameter d2 that is greater than the first average pore diameter d1 (i.e., d2>d1) extend along a length of the intervertebral cage. As depicted in FIGS. 11A-11B, the second portion 105 may extend from the posterior end 112 towards the anterior end 122. Also, the first portion 103 is positioned between the second portion 105 and the anterior end 122. In embodiments, the length of the intervertebral cage 10 comprises a posterior second portion 105 extending from the posterior end 112 towards the anterior end 122, an anterior second portion 105 extending from the anterior end 122 towards the posterior end 112, and a first portion 103 positioned between the posterior and anterior second portions 105. Accordingly, a porosity gradient is provided along the length (X direction) of the intervertebral cage 10 with a first portion 103 with porosity having the first average pore diameter d1 sandwiched between posterior and anterior second portions 105 with porosity having the first average pore diameter d2 that is greater than the second average pore diameter d1.

Although FIGS. 2A-11B only depict a porosity gradient along a single direction of the intervertebral cage 10, it is understood that the intervertebral cage may include a porosity gradient along multiple directions of the intervertebral cage 10. For example and without limitation, the intervertebral cage 10 may have a porosity gradient along a thickness of at least one of the side walls 100, posterior wall 110 and/or anterior wall 120, and a porosity gradient along a length of the intervertebral cage 10. In the alternative, the intervertebral cage 10 may have a porosity gradient along a thickness of at least one of the side walls 100, posterior wall 110 and/or anterior wall 120, and a porosity gradient along a width of the intervertebral cage 10. In another alternative, the intervertebral cage 10 may have a porosity gradient along a length of the intervertebral cage 10 and along a width of the intervertebral cage 10. In still another alternative, the intervertebral cage 10 may have a porosity gradient along a thickness of at least one of the side walls 100, posterior wall 110 and/or anterior wall 120, a porosity gradient along a length of the intervertebral cage 10, and a porosity gradient along a width of the intervertebral cage 10.

In use, the intervertebral cage 10 is implanted between a pair of adjacent vertebrae during a spine surgery operation.

The open inner core region 140 may include allograft or autograft bone material before the intervertebral cage 10 is implanted between a pair of adjacent vertebrae. In the alternative, or in addition to, allograft or autograft bone material may be placed in the open inner core region 140 after the intervertebral cage 10 is implanted between a pair of adjacent vertebrae, e.g., by inserting the allograft or autograft bone material through at least one of the apertures 101 in the side walls 100. The porosity gradient within the intervertebral cage 10 enhances the flow of bodily fluids and bone material into the intervertebral cage and promotes bone ingrowth and fusion between adjacent vertebrae. In some embodiments, the porosity gradient provides for porosity that may generally match or mimic porosity of bone material (i.e., the porosity in volume percent and/or average pore diameter) in contact with the intervertebral cage 10. Particularly, the intervertebral cage 10 may include a first portion 103 with porosity that general match's porosity of osteon (compact) bone material in contact with the first portion 103 and a second portion 105 with porosity that general matches porosity of cancellous (spongy) bone material in contact with the second portion 105. In this manner the intervertebral cage 10 provides portions with porosity that match different types of bone material thereby promoting bone ingrowth and fusion between adjacent vertebrae.

The intervertebral cage 10 may be formed or manufactured using any technique, process, etc., used to form porous bodies including without limitation 3D printing, electric discharge machining (EDM), mechanical machining, chemical etching, layer-by-layer processes, and the like. The intervertebral cage 10 may be formed from any material suitable for medical implants. Non-limiting examples include Non-limiting examples of suitable materials include metallic materials such as titanium, titanium alloys, tantalum, tantalum alloys, stainless steel alloys, and cobalt-chromium alloys, polymer materials such as polyethylene (PE) and polyether ether ketone (PEEK), and ceramic materials such as hydroxyapatite (HAP) $Ca_{10}(PO_4)_6(OH)_2$, tricalcium phosphate $Ca_3(PO_4)_2$, and mixtures of hydroxyapatite and tricalcium phosphate.

The intervertebral cages described herein may be used to promote bone ingrowth and fusion between adjacent vertebrae during and after a spine surgical procedure. In some embodiments, the porosity gradient enhances the flow of fluids, nutrients, additives, etc., in the thickness direction (Y direction) of the side walls 100. For example, the first average pore diameter d1 and/or the second average pore diameter d2 may be configured to wick fluids, nutrients additives, etc., from the upper surface 102 and the lower surface 104 through the upper and lower first portions 103, respectively, towards the second portion 105 positioned between the upper and lower first portions 103 (FIGS. 2A-2B). In the alternative, the first average pore diameter d1 and/or the second average pore diameter d2 may be configured to wick fluids, nutrients additives, etc., from the upper surface 102 and the lower surface 104 through the upper and lower second portions 105, respectively, towards the first portion 103 positioned between the upper and lower second portions 105 (FIGS. 3A-3B). Also, the first average pore diameter d1, the second average pore diameter d2 and the third average pore diameter d3 may be configured to wick fluids, nutrients additives, etc., from the lower surface 104 towards the upper surface 102 through the second portion 105, third portion 107 and first portion 103 (FIGS. 4A-4B), or wick fluids, nutrients additives, etc., from the upper surface 102 towards the lower surface 104 through the second portion 105, third portion 107 and first portion 103 (FIGS. 5A-5B).

In other embodiments, the porosity gradient enhances the flow of fluids, nutrients, additives, etc., through the width direction (Z direction) of the side walls 100. For example, the first average pore diameter d1 and/or the second average pore diameter d2 may be configured to wick fluids, nutrients additives, etc., from the outer surface 106 and the inner surface 108 through the outer and inner first portions 103, respectively, towards the second portion 105 positioned between the outer and inner first portions 103 (FIGS. 6A-6B). In the alternative, the first average pore diameter d1 and/or the second average pore diameter d2 may be configured to wick fluids, nutrients additives, etc., from the outer surface 106 and the inner surface 108 through the outer and inner second portions 105, respectively, towards the first portion 103 positioned between the outer and inner second portions 105 (FIGS. 7A-7B). Also, the first average pore diameter d1, the second average pore diameter d2 and the third average pore diameter d3 may be configured to wick fluids, nutrients additives, etc., from the inner surface 108 towards the outer surface 106 through the second portion 105, third portion 107 and first portion 103 (FIGS. 8A-8B), or wick fluids, nutrients additives, etc., from the outer surface 106 towards the inner surface 108 through the second portion 105, third portion 107 and first portion 103 (FIGS. 9A-9B).

In still other embodiments, the porosity gradient enhances the flow of fluids, nutrients, additives, etc., through the length direction (X direction) of the outer frame 12. For example, the first average pore diameter d1 and/or the second average pore diameter d2 may be configured to wick fluids, nutrients additives, etc., from the posterior end 112 and the anterior end 122 through the posterior and anterior first portions 103, respectively, towards the second portion 105 positioned between the posterior and anterior first portions 103 (FIGS. 10A-10B). In the alternative, the first average pore diameter d1 and/or the second average pore diameter d2 may be configured to wick fluids, nutrients additives, etc., from the posterior end 112 and the anterior end 122 through the posterior and anterior second portions 105, respectively, towards the first portion 103 positioned between the posterior and anterior second portions 105 (FIGS. 10A-10B).

The terms "upper" and "lower" refer to orientations depict in the drawings and are not meant to define exact orientations of intervertebral cages described herein. Also, the terms "generally" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

The invention claimed is:

1. An intervertebral cage comprising:
    an outer frame with an outer surface and an open inner core region defining an inner core surface, the outer frame further comprising superior and inferior surfaces and proximal and distal ends; and
    a porosity gradient within the outer frame with at least a portion of both the outer and inner core surfaces being porous;
    wherein the outer frame comprises a predefined and regular pattern of apertures that form the porosity gradient within the outer frame;
    wherein the superior and inferior surfaces each have a set of retention features; and
    wherein the intervertebral cage is shaped to facilitate placement of the intervertebral cage between two vertebrae.

2. The intervertebral cage of claim 1, wherein the outer frame comprises a plurality of layers with a predefined and regular pattern of apertures bonded to each other such that the predefined and regular pattern of apertures in each of the plurality of layers forms the porosity gradient within the outer frame.

3. The intervertebral cage of claim 2, wherein the porosity gradient comprises at least one of: an increasing average pore diameter in a direction from the posterior wall to a central portion of at least one of the pair of side walls and in a direction from the anterior wall to the central portion of at least one of the pair of side walls; and a decreasing average pore diameter in a direction from the posterior wall to a central portion of at least one of the pair of side walls and in a direction from the anterior wall to the central portion of at least one of the pair of side walls.

4. The intervertebral cage of claim 1, wherein the outer frame comprises a plurality of bonded layers, each layer having a predefined and regular pattern of apertures prior to bonding such that altogether the predefined and regular pattern of apertures in each layer of the plurality of layers forms the porosity gradient within the outer frame.

5. The intervertebral cage of claim 1, wherein the outer frame comprises a pair of side walls extending between the posterior wall and the anterior wall.

6. The intervertebral cage of claim 5, wherein the porosity gradient extends through at least one of the pair of side walls of the outer frame.

7. The intervertebral cage of claim 5, wherein the porosity gradient comprises a decreasing average pore diameter in a direction from an outer surface to an inner surface of at least one of the pair of side walls.

8. The intervertebral cage of claim 5, wherein the porosity gradient comprises an increasing average pore diameter in a direction from an outer surface to an inner surface of at least one of the pair of side walls.

9. The intervertebral cage of claim 5, wherein the porosity gradient comprises a decreasing average pore diameter in a direction from an upper surface to a lower surface of at least one of the side walls.

10. The intervertebral cage of claim 5, wherein the porosity gradient comprises an increasing average pore diameter in a direction from an upper surface to a lower surface of at least one of the side walls.

11. The intervertebral cage of claim 5, wherein the porosity gradient comprises a decreasing average pore diameter in a direction from the posterior wall to the anterior wall of the outer frame.

12. The intervertebral cage of claim 5, wherein the porosity gradient comprises an increasing average pore diameter in a direction from the posterior wall to the anterior wall of the outer frame.

13. The intervertebral cage of claim 1, wherein the porosity gradient comprises a first portion with a porosity within a range of about 5% by volume to about 30% by volume and a second portion within a range of about 30% by volume to about 90% by volume.

14. The intervertebral cage of claim 1, wherein the porosity gradient comprises a first portion with a porosity with an average diameter between about 5 µm and about 100µ and a second portion with a porosity with an average diameter between about 100 µm and 1000 µm.

15. An intervertebral cage comprising: an outer frame comprising:
    a superior surface, an inferior surface, a posterior wall, an anterior wall and a pair of side walls extending between the anterior wall and the posterior wall;
    an open inner core region between the posterior wall, the anterior wall, and the pair of side walls; and
    a porosity gradient within at least one of the posterior wall, the anterior wall, and the pair of side walls;
    wherein the porosity gradient promotes bone ingrowth and fusion between adjacent vertebrae;
    wherein the outer frame comprises a predefined and regular pattern of apertures that forms the porosity gradient within the outer frame;
    wherein the superior and inferior surfaces each have a set of retention features; and
    wherein at least one of the anterior wall and posterior wall is not the same length as the pair of side walls.

16. The intervertebral cage of claim 15, wherein the porosity gradient comprises a first portion with a porosity within a range of about 5% by volume to about 30% by volume and a second portion within a range of about 30% by volume to about 90% by volume.

17. The intervertebral cage of claim 15, wherein the porosity gradient comprises a first portion with a porosity with an average diameter between about 5 µm and about 100µ and a second portion with a porosity with an average diameter between about 100 µm and 1000 µm.

18. The intervertebral cage of claim 15, wherein the porosity gradient is selected from at least of: a decreasing average pore diameter in a direction from an outer surface to an inner surface of at least one of the pair of side walls; an increasing average pore diameter in a direction from an outer surface to an inner surface of at least one of the pair of side walls; a decreasing average pore diameter in a direction from an upper surface to a lower surface of at least one of the side walls; and an increasing average pore diameter in a direction from an upper surface to a lower surface of at least one of the side walls.

19. The intervertebral cage of claim 15, wherein at least a portion of the outer frame is formed using at least one of the following: 3D printing, electric discharge machining, mechanical machining, etching, chemical etching, and layer-by-layer processes.

20. The intervertebral cage of claim 15, further comprising at least one aperture between the open inner core region and an exterior surface of the intervertebral cage.

* * * * *